United States Patent
Biber et al.

(10) Patent No.: US 8,805,477 B2
(45) Date of Patent: Aug. 12, 2014

(54) METHOD FOR USE OF A COMMON SHOULDER COIL PART FOR BOTH LEFT AND RIGHT SHOULDER

(71) Applicants: Stephan Biber, Erlangen (DE); Zeng He He, ShenZhen (CN); Jian Min Wang, ShenZhen (DE)

(72) Inventors: Stephan Biber, Erlangen (DE); Zeng He He, ShenZhen (CN); Li Ma, ShenZhen (CN); Hai Ning Wang, ShenZhen (CN); Jian Min Wang, ShenZhen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/060,739

(22) Filed: Oct. 23, 2013

(65) Prior Publication Data

US 2014/0051982 A1    Feb. 20, 2014

Related U.S. Application Data

(62) Division of application No. 12/770,901, filed on Apr. 30, 2010, now abandoned.

(30) Foreign Application Priority Data

Apr. 30, 2009   (CN) .......................... 2009 1 0135866

(51) Int. Cl.
    *A61B 5/055*    (2006.01)

(52) U.S. Cl.
    USPC .......................................... 600/422; 324/318

(58) Field of Classification Search
    USPC .......... 600/410, 422, 423; 324/307, 309, 318, 324/322
    See application file for complete search history.

(56) References Cited

U.S. PATENT DOCUMENTS 7,031,763 B1 *   4/2006   Zhang ........................... 600/422
2009/0121715 A1 *   5/2009   Guan et al. .................... 324/318

* cited by examiner

*Primary Examiner* — Ruth S Smith
(74) *Attorney, Agent, or Firm* — Schiff Hardin LLP

(57) ABSTRACT

In a method for acquiring magnetic resonance signals from a first shoulder or an opposite second shoulder of a patient, a shoulder coil anterior part and a shoulder coil posterior part are provided. A base plate is engageable with a moveable support element connecting the shoulder coil posterior part to the base plate to permit lateral movement and 90 degree rotation of the shoulder coil posterior part. With the base plate beneath the patient, the shoulder coil posterior part is placed below the first shoulder and the shoulder coil anterior part is placed above the first shoulder to permit acquisition of magnetic resonance measurements. To acquire signals from the opposite second shoulder, the shoulder coil posterior part is moved across the base plate to be positioned beneath the second shoulder and is rotated by 90 degrees. The shoulder coil anterior part is placed above the rotated shoulder coil posterior part.

2 Claims, 6 Drawing Sheets

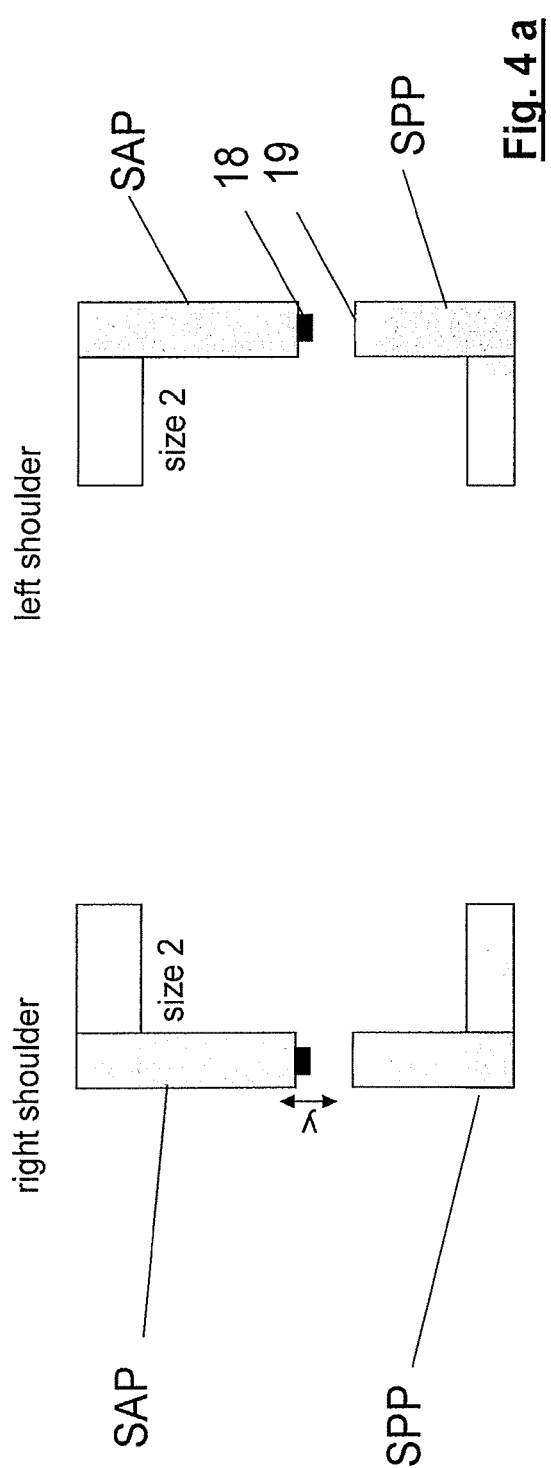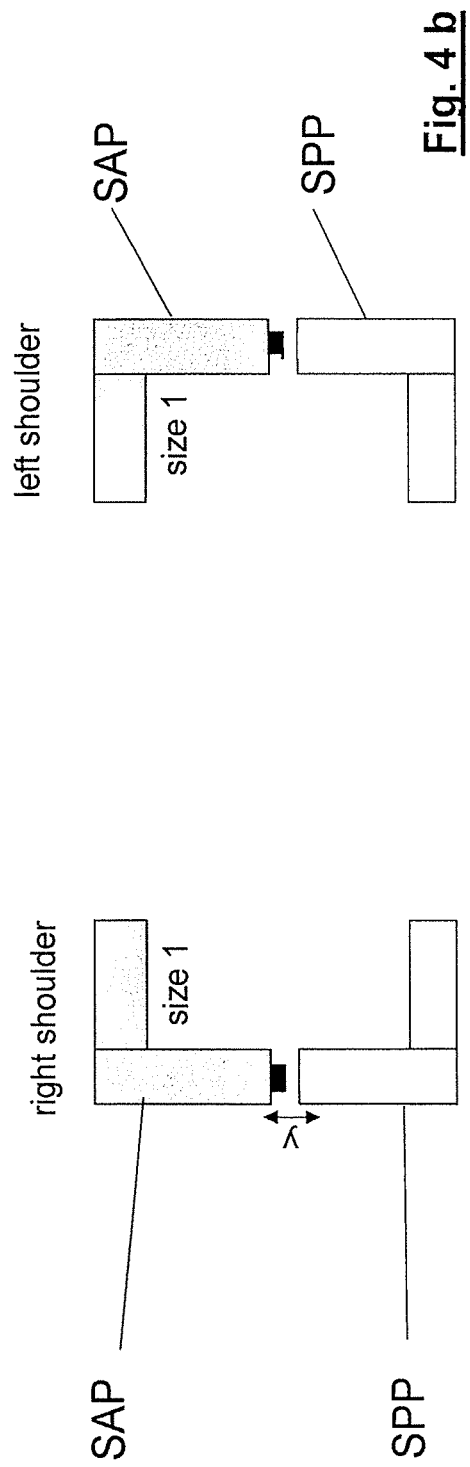
Fig. 4 a
Fig. 4 b

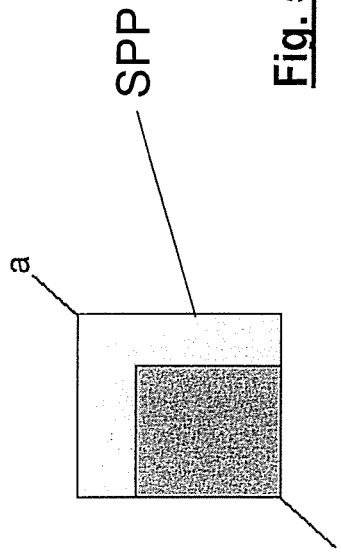
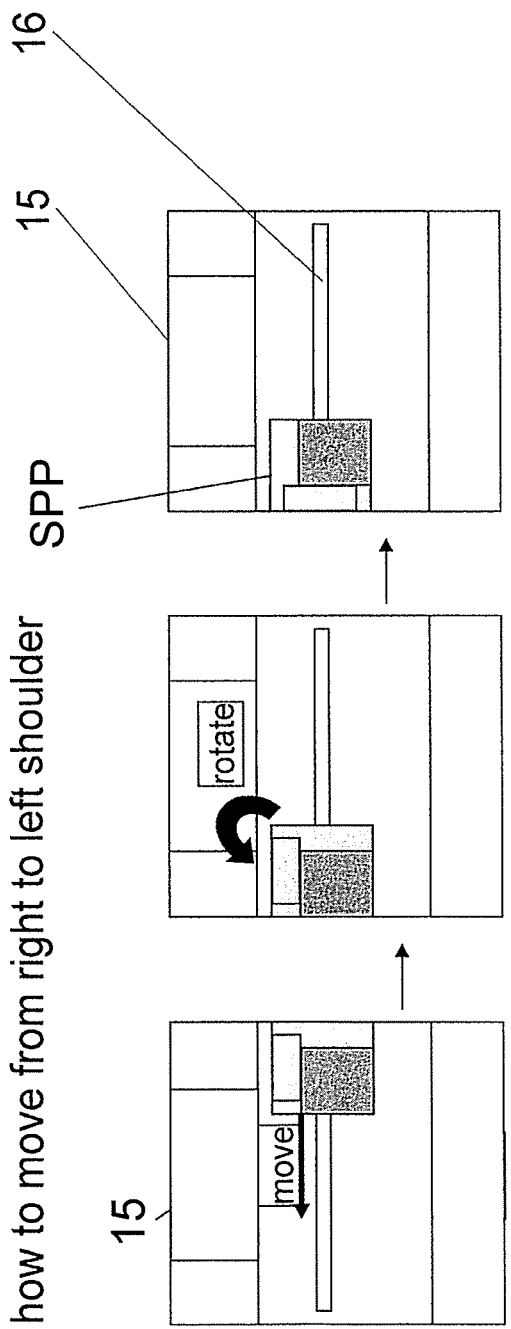

METHOD FOR USE OF A COMMON SHOULDER COIL PART FOR BOTH LEFT AND RIGHT SHOULDER

CROSS-REFERENCE TO RELATED APPLICATIONS

This application is a divisional of U.S. application Ser. No. 12/770,901, filed Apr. 30, 2010, the entire contents of which is hereby incorporated by reference herein.

BACKGROUND OF THE INVENTION

1. Field of the Invention

The present invention concerns a local coil for acquiring magnetic resonance (MR) data from a shoulder of a patient, an MR apparatus and a method for use of a shoulder coil.

2. Description of the Prior Art

Magnetic resonance tomography (MRT), also called magnetic resonance imaging (MRI), is known e.g. from DE10314215B4.

Modern magnetic resonance systems normally operate with a number of various RF antennas (called coils in the following) for transmission and reception of radio-frequency pulses for exciting nuclei so as to emit magnetic resonance signals and/or for acquisition of the induced magnetic resonance signals. A magnetic resonance system normally has a large whole-body coil (body coil) permanently installed in the magnetic resonance scanner. The whole-body coil is typically arranged cylindrically (for example with a structure known as a birdcage structure) around the patient acquisition chamber in which the patient is supported on a bed (often also called a patient positioning table) during the measurement.

For increasing the signal to noise ratio (SNR) in magnetic resonance imaging, most MRI scanners today use local coils. Local coils are receiving antennas, which are brought close to the region that shall be imaged. For many parts of the body, dedicated coils exist (e.g. shoulder coil, wrist coil, head coil, spine coil, invasive coils e.g. for prostate imaging, etc.). For imaging of a shoulder, today's MRI systems provide a dedicated shoulder coil. Because of economic reasons (cost, scan time, workflow) it is desirable for the local coil to be easily placed on the patient. At the same time, the coil shall be comfortable for the patient. An MRI coil usually consists of a mechanical housing, which houses the antennas (mostly loop or butterfly antennas) and the active electronics which usually consist of a low noise amplifier and tuning/detuning circuits for the antenna.

Conventional shoulder arrays have the shape of a shell e.g. according to FIGS. 2a and 2b. In order to allow the coil to be as close as possible to the imaged volume, different sizes of coils have been built, to account for the different anatomy (shoulder size) of the patient population. Another topic which has to be addressed is the fact that the coil shall be applicable to the left and to the right shoulder. Today this is done by "rotating" the coil 180° along the z-direction (z is parallel to the main magnetic field B0). One disadvantage of today's shoulder array design is the shell-like shape of the coil. This requires that after the patient has been placed on the table, either the patient has to move his/her shoulder into the coil or the coil has to be moved with respect to the patient. This is uncomfortable for the patient, it can be difficult especially for injured patients and is a time consuming step in the workflow. These are the major disadvantages of the shell-design of a shoulder coil.

SUMMARY OF THE INVENTION

An object of the invention is to improve positioning of a patient's shoulder in a shoulder coil.

According to one aspect the invention, the housing of the shoulder local coil arrangement has two (separate or separable) parts (which can be separated from each other).

According to a further aspect the invention an MRT includes a local coil arrangement designed to support the production of an MRT image of a shoulder, wherein the housing of the local coil arrangement is formed of two parts, wherein the distance of the parts is alterable.

A further aspect the invention an MRT is a method for producing an MRT image of a shoulder of a patient, wherein at least two parts of a local coil arrangement are positioned adjacent to the shoulder between them.

An improvement results in the mechanical and (partly) electrical design of a shoulder array made from an anterior and a posterior part and a mechanical construction that allows the coil to be adapted to various patient sizes and left and right shoulders while minimizing the number of components necessary for the coil. The minimization of the number of different components goes along with an optimization of the costs and improved workflow. The split design of the coil makes it obsolete for the patient to move into the coil with a sideward movement (x-direction, i.e. orthogonally to the y-direction and z-direction) or to move the coil sideward towards the patient. The patient can comfortably lie down on the SPP and when he/she is lying on the SPP, the SAP (shoulder anterior part) can be placed on top of the SPP. This improves patient comfort and workflow and therefore gives direct benefit for the customer.

In a preferred embodiment of the invention, the housing of the local coil arrangement is formed of at least three parts, of which only two are in use simultaneously.

In a further preferred embodiment of the invention, a first part (SPP=shoulder posterior part) is closer to the patient table on which the shoulder can be positioned, than a further part (SAP=shoulder anterior part).

In a further preferred embodiment of the invention, one part is connectable either to the patient table or to a base plate which itself is then connectable to or placed on the patient table.

In a further preferred embodiment of the invention, the first part and the further part are movable towards a patient to allow adjustment to the size of a shoulder of the patient.

In a further preferred embodiment of the invention, one part is available in at least two sizes, and this part can be exchanged by a part with a different size.

In a further preferred embodiment of the invention, there is a plane of symmetry in a shoulder coil, which plane allows use of the shoulder coil for a left shoulder as well as for a right shoulder of a patient.

In a further preferred embodiment of the invention, each part of the local coil has a coil antenna which can be connected via a connection to an image generation unit.

BRIEF DESCRIPTION OF THE DRAWINGS

Prior art

Prior art

FIGS. 3-6 respectively show different embodiments of the shoulder coils.

DESCRIPTION OF THE PREFERRED EMBODIMENTS

Figure 1:
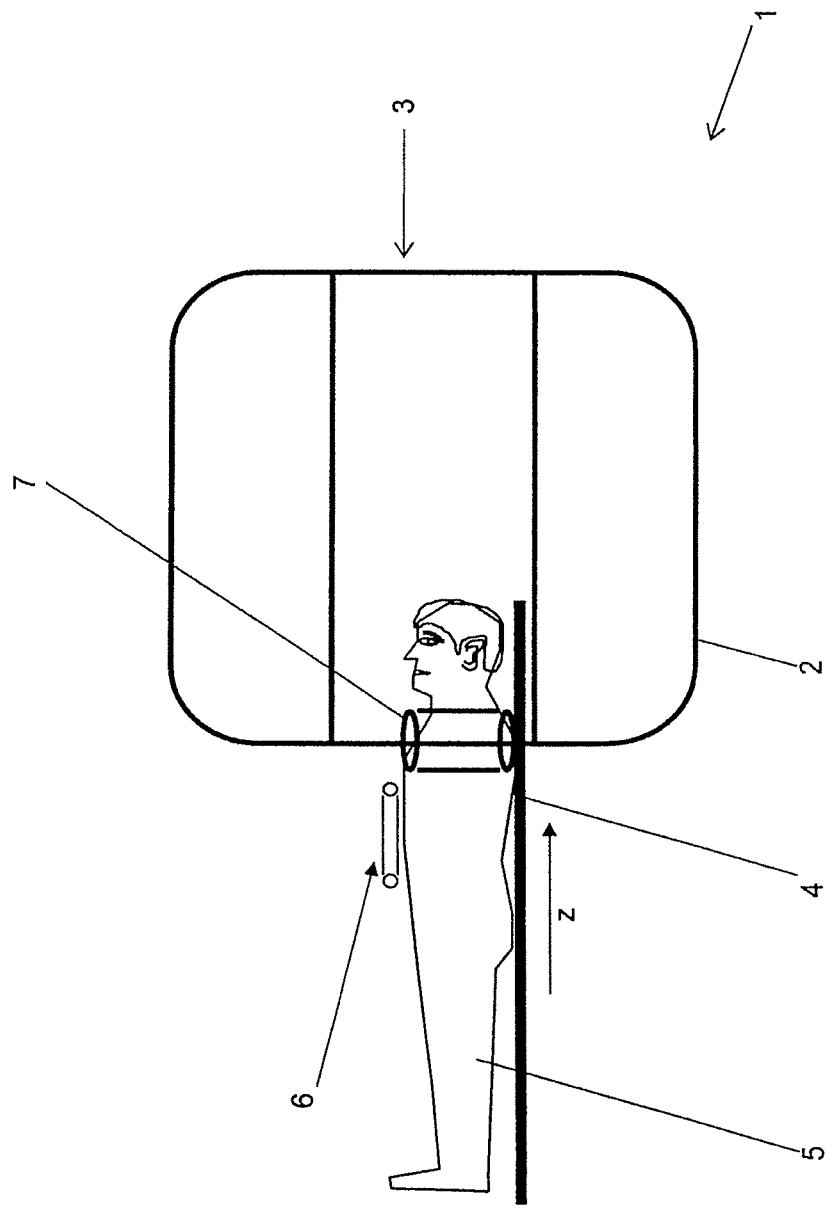
FIG. 1 shows a magnetic resonance tomography system.

FIG. 1 shows a magnetic resonance tomography (MRT) scanner (data acquisition unit) 1 has a basic field magnet 2 with a cylindrical tube 3 and a patient table 4 for moving a patient 5 into the cylindrical tube 3 of the MRT scanner 1. As is known the basic field magnet 2 has a body coil built therein or inserted therein. Local coils 6 or 7 can be used near an imaged volume of the body of the patient, e.g. a shoulder coil 7 for shoulder imaging.

Figure 2:
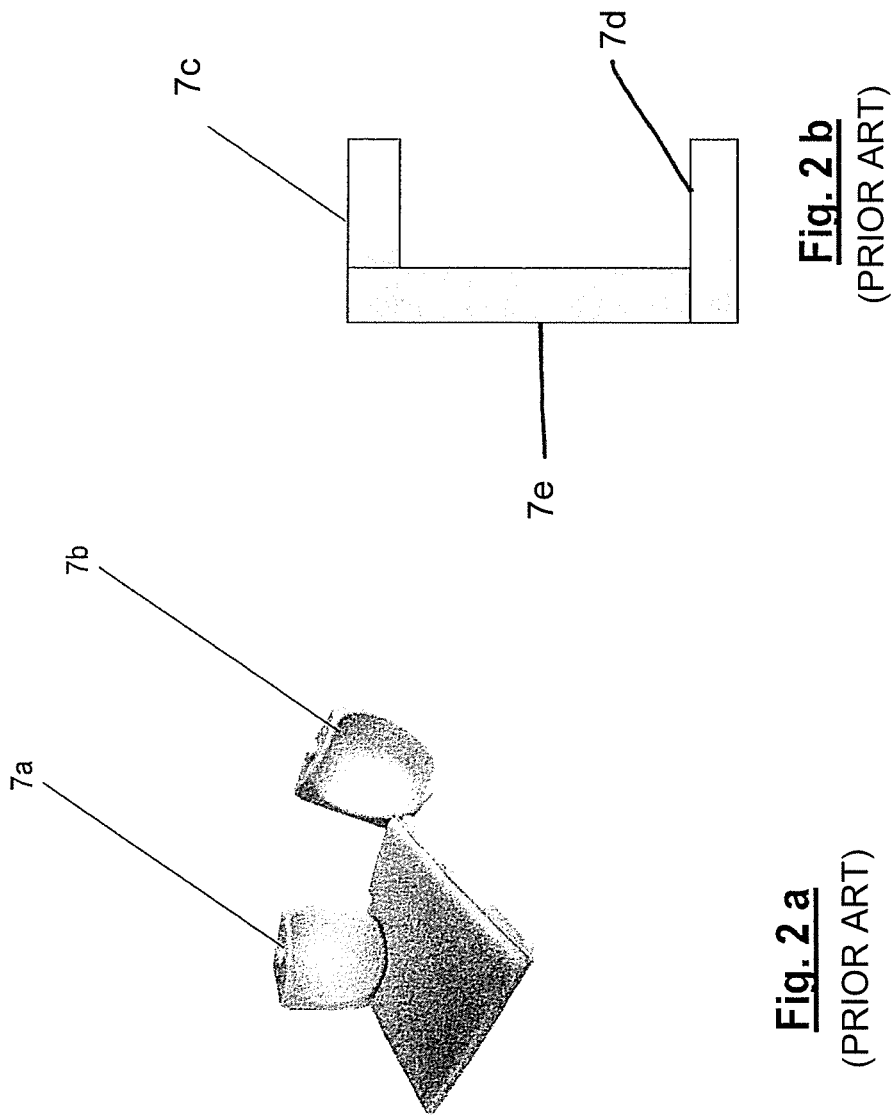
FIGS. 2a, 2b show known shoulder coils.

FIG. 2a shows known shoulder coils 7a, 7b that respectively can be positioned at the shoulder of a patient.

FIG. 2b shows the basic components of a known shoulder coil schematically, with an upper part 7c and a lower part 7d connected by an inseparable connector 7e.

FIGS. 3-6 show different embodiments of a shoulder coil. For a better understanding, the coils are shown very schematically, but of course they can have a roundish and soft surface design as the known design in FIG. 2a has (but according an embodiment of the invention as a two-part shoulder array).

The invention described herein allows shoulder imaging that overcomes the major drawbacks of today's approaches shown in FIGS. 2a, 2b. The basis of the invention is to split the housing of the shoulder coil in an upper (anterior) part and a lower (posterior) part.

In the following, the parts are called SAP (shoulder anterior part) and SPP (shoulder posterior part). The lower part (SPP) can be connected either to the patient table or to a base plate, which itself can be connected to or placed on the patient table.

Figure 3:
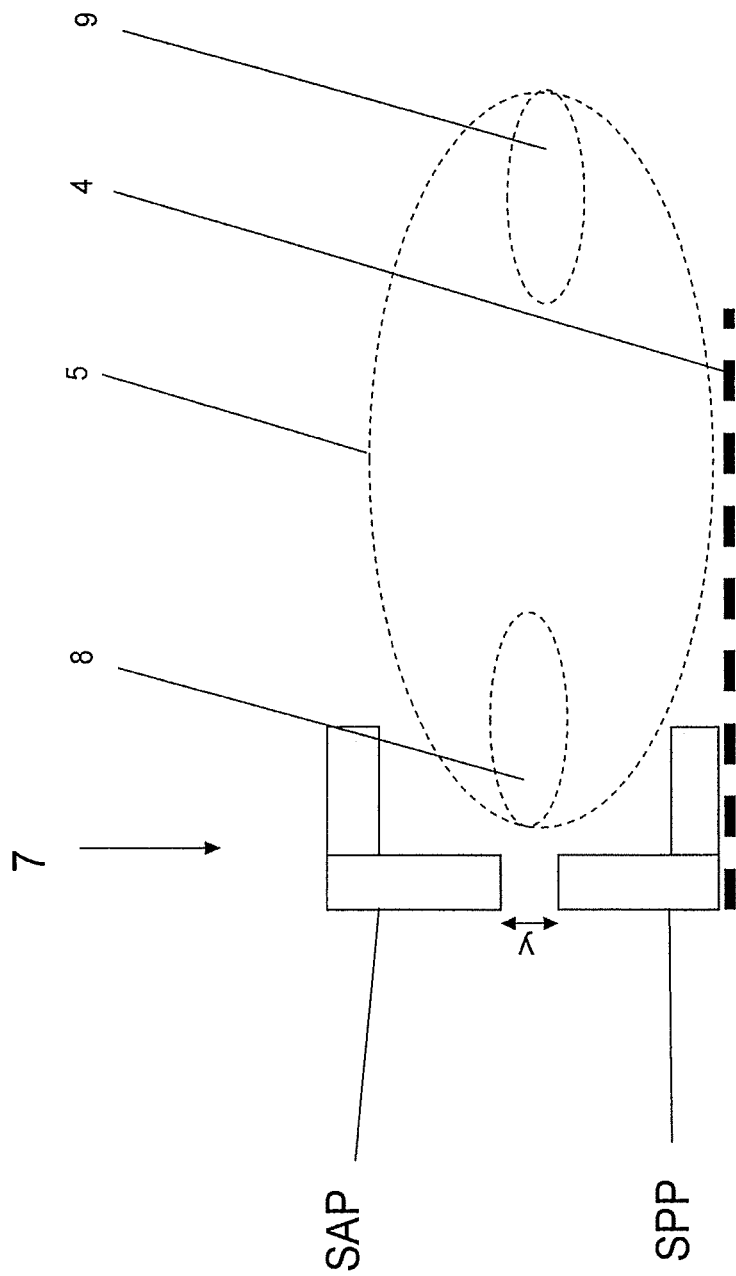

There are three preferred different approaches how a shoulder coil, made from an anterior and a posterior part can be designed mechanically:

According to the cross sectional view in FIG. 3, the parts SAP and SPP of a shoulder coil 7 are movable along the y-direction (indicated by arrow "y") to allow adjustment to the anatomy of a patient 5 on a table 4; one preferred solution is to have the anterior and the posterior part mechanically identical as in so that moving the shoulder coil parts from the right shoulder 8 to the left shoulder 9 allows using the SAP as the posterior part and the SPP as the anterior part (in FIG. 3 the patient 5 is laying on his back as shown for the same patient 5 in prior art FIG. 1 and with the patient's feet in front when viewing the plan view of FIG. 3).

According to the cross sectional views in FIGS. 4a and 4b, the parts SAP and SPP of a shoulder coil 7 are not movable in the y-direction (they can be connected in an adjacent position), but there are two different sizes (FIG. 4a size and FIG. 4b size) available for the upper part SAP (for the left and right upper part in FIGS. 4a and 4b), to allow adjustment to the anatomy of the patient 5.

The two upper parts SAP (for the left and right shoulder) in FIG. 4b are smaller than the two upper parts SAP (for the left and right shoulder) in FIG. 4a.

One possible derivative would be to allow the larger and the smaller part be used as the anterior part and the posterior part, just as required by the patient's anatomy, i.e. using the bigger part SAP in FIG. 4a as the lower posterior part and using the smaller part SPP in FIG. 4a as the upper anterior part.

The local coil parts SAP, SPP can be (separably) fixed to each other by engagement elements 18,19 that can also produce an electrical connection between the coil portions respectively contained in the coil parts SAP, SPP.

According to FIGS. 5a and 5b, to further improve the solution in FIGS. 4a and 4b an additional plane "a" of symmetry through each shoulder coil part SPP and SAP (shown for SPP as an example in FIG. 5a in elevated view) allows the shoulder coil part SPP to be used for different patient sizes and for left and right shoulders while minimizing the number of parts necessary for the shoulder coil.

A base plate 15 carries a shoulder coil part SPP, which is moved from the position according to FIG. 5b in the direction of the arrow "move" to the position in FIG. 5c and rotated according to arrow "rotate" to the position in FIG. 5d.

For example, a long groove 16 in the base plate 15 in which an element of the shoulder coil part SPP engages can support this movement and rotation.

The base plate 15 can be positioned on a patient table.

The additional plane "a" of symmetry added in the mechanics makes it also favorable to make the antenna design symmetrical and therefore does not only affect the mechanical construction but also can affect the electrical design.

Figure 6:
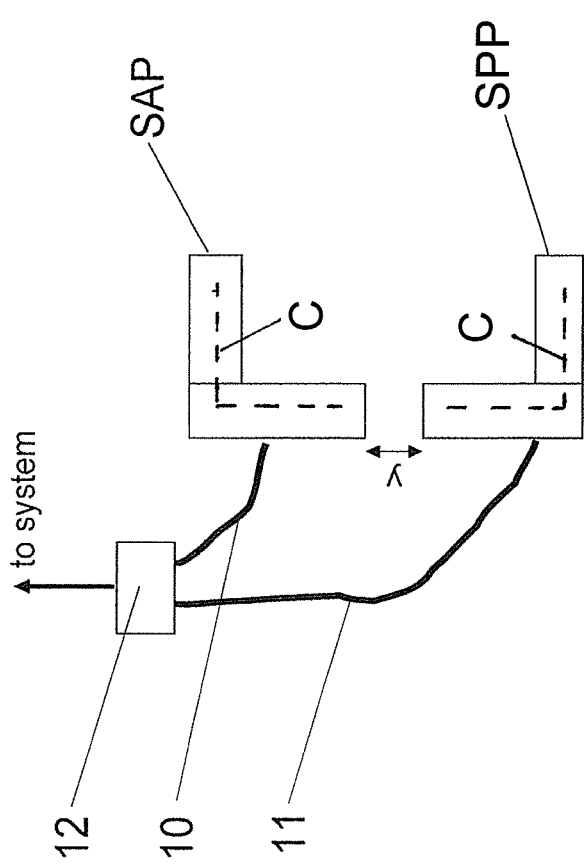

FIG. 6 shows wired connections 10, 11 of antennas in shoulder coil parts SPP and SAP, which respectively are connected to an interface box 12, that is connectable to a known MRI system for producing images based on e.g. detected local coil antenna signals. The outlines of SPP and SAP schematically illustrate respective housings of those components, and conductors C that form the shoulder coil antenna itself are schematically shown inside those housings.

Although modifications and changes may be suggested by those skilled in the art, it is the intention of the inventors to embody within the patent warranted hereon all changes and modifications as reasonably and properly come within the scope of their contribution to the art.

What is claimed is:

1. A method for selectively acquiring magnetic resonance signals from a first shoulder and an opposite second shoulder of a patient using a single shoulder coil arrangement, comprising the steps of:

providing a shoulder coil arrangement comprising a shoulder coil anterior part and a shoulder coil posterior part, the shoulder coil anterior and posterior parts each having a diagonal plane of symmetry passing through diagonally opposite corners of the respective parts, and providing a base plate connecting with the shoulder coil posterior part in movable fashion so as to permit lateral movement of the shoulder coil posterior part laterally across the base plate and also to permit a 90° rotational movement of the shoulder coil posterior part about a vertical axis perpendicular to the base plate;

with the base plate positioned beneath the patient placing the shoulder coil posterior part below the first shoulder of the patient, placing the shoulder coil anterior part above the shoulder coil posterior part at an opposite side of the first shoulder of the patient and then acquiring said magnetic resonance signals as to said first shoulder; and moving the shoulder coil posterior part laterally across the base plate to be positioned beneath the second shoulder of the patient, rotating the shoulder coil posterior part by 90° about said perpendicular axis, placing the shoulder coil anterior part above the rotated coil posterior part at an opposite side of said second shoulder, and then acquiring said magnetic resonance signals as to said second shoulder.

2. The method of claim 1 wherein the base plate includes a groove for connecting the base plate to the shoulder coil posterior part.

* * * * *